US00PP27209P3

(12) United States Plant Patent
Braeunig

(10) Patent No.: US PP27,209 P3
(45) Date of Patent: Sep. 27, 2016

(54) ***PETUNIA* PLANT NAMED 'FLORTUNBLUVE'**

(50) Latin Name: *Petunia×hybrida*
Varietal Denomination: Flortunbluve

(71) Applicant: Florensis B.V., Hendrik-Ido-Ambacht (NL)

(72) Inventor: Tobias Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 14/545,609

(22) Filed: May 28, 2015

(65) Prior Publication Data

US 2016/0212909 P1 Jul. 21, 2016

Related U.S. Application Data

(60) Provisional application No. 62/125,394, filed on Jan. 20, 2015.

(51) Int. Cl.
*A01H 5/02* (2006.01)

(52) U.S. Cl.
USPC ..... Plt./356.2

(58) Field of Classification Search
USPC ..... Plt./356.2
See application file for complete search history.

*Primary Examiner* — Annette Para
(74) *Attorney, Agent, or Firm* — Audrey Charles

(57) ABSTRACT

A new and distinct cultivar of *Petunia* plant named 'Flortunbluve', characterized by its light violet-colored flowers having dark violet-colored venation, medium green-colored foliage, and moderately vigorous, compact, semi-upright growth habit, is disclosed.

1 Drawing Sheet

Latin name of genus and species of plant claimed: *Petunia× hybrida* .

Variety denomination: 'Flortunbluve'.

BACKGROUND OF THE INVENTION

The present invention relates to a new and distinct cultivar of *Petunia* plant botanically known as *Petunia×hybrida* and hereinafter referred to by the cultivar name 'Flortunbluve'.

The new cultivar originated in a controlled breeding program in Quedlinburg, Germany during August 2007. The objective of the breeding program was the development of *Petunia* cultivars with single-type flowers, unique flower coloration and patterns, and compact, semi-upright growth habit.

The new *Petunia* cultivar is the result of cross-pollination. The female (seed) parent of the new cultivar is the proprietary *Petunia×hybrida* breeding selection coded 8173-1, not patented, characterized by its white-colored flowers having medium violet-colored venation, medium green-colored foliage, and moderately vigorous, semi-upright growth habit. The male (pollen) parent of the new cultivar is the proprietary *Petunia×hybrida* breeding selection coded 3422-1, not patented, characterized by its white-colored flowers having medium violet-colored venation, medium green-colored foliage, and moderately vigorous, semi-upright growth habit. The new cultivar was discovered and selected as a single flowering plant within the progeny of the above stated cross-pollination during August 2008 in a controlled environment in Quedlinburg, Germany.

Asexual reproduction of the new cultivar by terminal stem cuttings since August 2008 in Quedlinburg, Germany; Arroyo Grande, Calif.; and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Flortunbluve' as a new and distinct cultivar of *Petunia* plant:

1. Light violet-colored flowers having dark violet-colored venation;
2. Medium green-colored foliage; and
3. Moderately vigorous, compact, semi-upright growth habit.

Plants of the new cultivar differ from plants of the female and male parents primarily in intensity of flower venation color.

Of the many commercially available *Petunia* cultivars, the most similar in comparison to the new cultivar is POTUNIA Piccola Blue Ice 'Duepotpiblic', U.S. Plant Pat. No. 23,810. However, in side by side comparisons, plants of the new cultivar differ from plants of 'Duepotpiblic' in at least the following characteristics:

1. Plants of the new cultivar have larger leaves than plants of 'Duepotpiblic'; and
2. Plants of the new cultivar have a larger corolla diameter than plants of 'Duepotpiblic'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Flortunbluve'. The plants were grown in 4-inch pots for 4 weeks in a greenhouse in West Chicago, Ill.

DETAILED BOTANICAL DESCRIPTION

Figure 1:
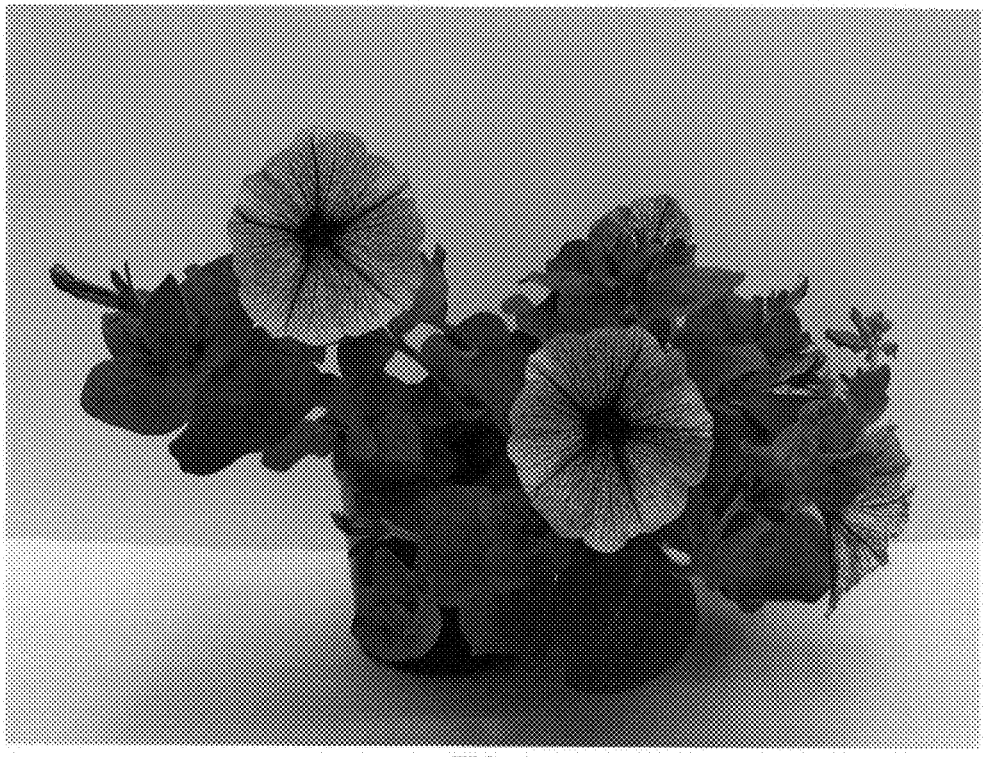
FIG. 1 illustrates a side view of the overall growth and flowering habit of 'Flortunbluve'.
Figure 2:
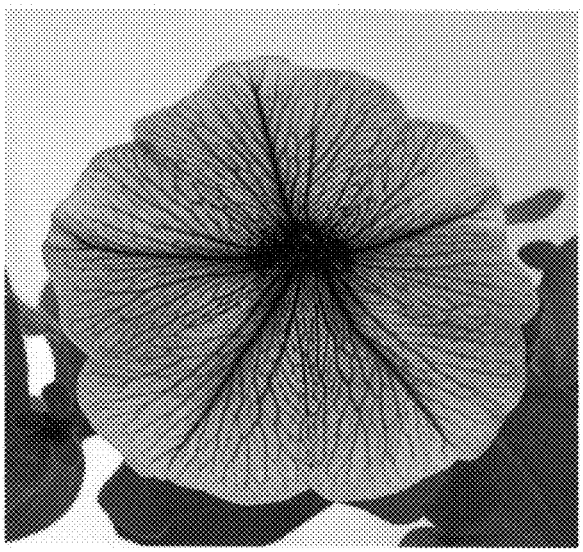
FIG. 2 illustrates a close-up view of an individual flower of 'Flortunbluve'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2015 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 5 weeks utilizing a soilless growth medium. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Petunia×hybrida* cultivar Flortunbluve.

Parentage:

*Female parent*.—Proprietary *Petunia×hybrida* breeding selection coded 8173-1, not patented.

*Male parent*.—Proprietary *Petunia×hybrida* breeding selection coded 3422-1, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Moderately vigorous, compact, semi-upright.

*Size*.—Height from soil level to top of plant plane: Approximately 16.0 cm. Width: Approximately 55.0 cm.

*Branching habit*.—Freely branching, pinching improves basal branching. Quantity of main branches per plant: Approximately 3.

*Branch*.—Strength: Moderate. Length: Approximately 24.0 cm. Diameter: Approximately 5.0 mm. Length of central internode: Approximately 2.5 cm. Texture: Densely glandular pubescent with a mixture of long and short hairs. Gland color: Colorless. Color of young and mature stems: 144A.

Foliage description:

*General description*.—Quantity of leaves per main branch: Approximately 14. Fragrance: Slight. Form: Simple. Arrangement on flowering stem: Opposite.

*Leaves*.—Aspect: Acute angle to stem. Shape: Ovate to elliptic. Margin: Entire. Apex: Acute. Base: Attenuate. Venation pattern: Pinnate. Length of mature leaf: Approximately 6.2 cm. Width of mature leaf: Approximately 5.7 cm. Texture of upper and lower surfaces: Sparsely glandular pubescent. Gland color: Colorless. Color of upper surface of young and mature foliage: 137A with venation of 146D to indistinguishable. Color of lower surface of young and mature foliage: Closest to 138B with venation of 146D to indistinguishable.

*Petiole*.—Length: Approximately 2.0 mm. Width: Approximately 4.0 mm. Texture: Sparsely glandular pubescent with a mixture of long and short hairs. Gland color: Colorless. Color: 146D.

Flowering description:

*Flowering habit*.—'Flortunbluve' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 11. Fragrance: None detected.

*Bud*.—Rate of opening: Generally takes 2 to 3 days for bud to progress from first color to fully open flower. Quantity per plant: Approximately 10.

*Bud just before opening*.—Shape: Oblong. Length: Approximately 3.7 cm. Diameter at apex: Approximately 7.0 mm. Diameter at base: Approximately 2.0 mm. Texture: Densely glandular pubescent with a mixture of long and short hairs. Gland color: Colorless. Color of petals: 145D with venation of N77A. Color of tube: 145B with venation of N77A.

*Corolla*.—Diameter: Approximately 6.7 cm.

*Petals*.—Quantity: 5, fused to form a tube. Shape: Obovate. Appearance: Dull. Margin: Entire, slightly wavy. Apex: Acute. Length from tube: Approximately 3.4 to 3.5 cm. Length of free portion: Approximately 1.3 cm. Width: Approximately 3.4 cm. Texture of upper surface: Glabrous. Texture of lower surface: Sparsely glandular pubescent. Gland color: Colorless. Color of upper surface when first open: 85A with heavy venation of close to 86A. Color of lower surface when first open: 85C to 85D with venation of 86B and midveins of N77A. Color of upper surface when fully open: 85A to 85B with heavy venation of close to 86A. Color of lower surface when fully open: 85C to 85D with venation of 86B to 86C and midveins of N77A.

*Corolla tube*.—Length: Approximately 3.0 cm. Diameter at distal end: Approximately 1.0 cm. Diameter at proximal end: Approximately 3.0 mm. Texture of inner surface: Glabrous. Texture of outer surface: Densely glandular pubescent with a mixture of long and short hairs. Gland color: Colorless. Color of inner surface: 85A to 85B with venation of close to 86A and N186A. Color of outer surface: 79D with venation of N77A.

*Sepals*.—Quantity per flower: 5, fused at base. Shape: Linear. Apex: Acute. Length: Approximately 1.8 cm. Width: Approximately 5.0 mm. Texture of upper and lower surfaces: Densely glandular pubescent. Gland color: Colorless. Color of upper surface: 137A. Color of lower surface: 137B transitioning to 144B at base.

*Peduncle*.—Strength: Strong, flexible. Aspect: Acute angle to stem. Length: Approximately 3.5 cm. Diameter: Approximately 2.0 mm. Texture: Densely glandular pubescent with a mixture of long and short hairs. Gland color: Colorless. Color: 144A often tinted with 187B from sun.

*Reproductive organs*.—Androecium: Stamen quantity: 5, basifixed. Stamen length: Approximately 2.3 cm. Filament length of fixed portion: Approximately 9.0 mm. Filament color: NN155A. Anther shape: Bilobed. Anther length: Approximately 1.0 mm. Anther color: 161D. Pollen amount: Moderate. Pollen color: 155D. Gynoecium: Pistil quantity: 1 per flower. Pistil length: Approximately 2.4 cm. Stigma shape: Funnel. Stigma length: Approximately 1.0 mm. Stigma color: 146A with funnel portion of 79C. Style length: Approximately 1.9 cm. Style color: 145C. Ovary length: Approximately 4.0 mm. Ovary color: 144B.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Flortunbluve', substantially as herein illustrated and described.

* * * * *